(12) United States Patent
Thiel et al.

(10) Patent No.: US 8,280,152 B2
(45) Date of Patent: Oct. 2, 2012

(54) METHOD FOR OPTICAL MEASUREMENT OF THE THREE DIMENSIONAL GEOMETRY OF OBJECTS

(75) Inventors: Frank Thiel, Ober-Ramstadt (DE); Joachim Pfeiffer, Behsheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 181 days.

(21) Appl. No.: 12/770,426

(22) Filed: Apr. 29, 2010

(65) Prior Publication Data

US 2010/0209002 A1 Aug. 19, 2010

Related U.S. Application Data

(63) Continuation of application No. PCT/EP2008/065626, filed on Nov. 14, 2008.

(30) Foreign Application Priority Data

Nov. 15, 2007 (DE) .................. 10 2007 054 906

(51) Int. Cl.
*G06K 9/00* (2006.01)
(52) U.S. Cl. ........ 382/154; 345/426; 356/603; 356/617; 382/203; 382/206
(58) Field of Classification Search .................. 345/426; 356/603, 617; 382/154, 203; 702/167
See application file for complete search history.

(56) References Cited

U.S. PATENT DOCUMENTS

| 4,615,678 A | 10/1986 | Moermann et al. |
| 5,135,308 A | 8/1992 | Kuchel |
| 5,818,959 A * | 10/1998 | Webb et al. .................. 382/154 |

(Continued)

FOREIGN PATENT DOCUMENTS

CA 2 519 075 A1 7/2004

(Continued)

OTHER PUBLICATIONS

Guhring, J., a dissertation, "3D Erfassung und Objektrekonstruktion mittels Streifenprojektion" (University of Stuttgart, 2002) with English abstract attached.

*Primary Examiner* — Gregory M Desire
(74) *Attorney, Agent, or Firm* — Fitzpatrick, Cella, Harper & Scinto

(57) ABSTRACT

The invention relates to a method for optically scanning the three-dimensional geometry of an object by means of triangulation, in which a pattern (9, 9') is projected onto the object (7) to be scanned in order to obtain a 3D data set, and the projected pattern (9, 9') is recorded in an image (40, 41). In a first step for the production of at least one first image (40), a first pattern (9) is projected and in a second step for the creation of at least one further image (40), a further pattern (9') deviating from the first as regards position or shape is projected onto the object (7) to be scanned and the image (41) is created. The first image (40) and the further image (41) comprise at least one common point (44). The 3D data acquired from the images (40, 41) are merged in a subsequent step on the basis of the 3D data of the at least one common point (44) such that the 3D data acquired from said images (40, 41) agree at least with reference to the 3D data of the common point (44) in the 3D data set.

11 Claims, 3 Drawing Sheets

U.S. PATENT DOCUMENTS

| | | | |
|---|---|---|---|
| 5,946,645 A | 8/1999 | Rioux et al. | |
| 6,219,063 B1* | 4/2001 | Bouguet et al. | 345/426 |
| 6,542,249 B1 | 4/2003 | Kofman et al. | |
| 6,549,288 B1* | 4/2003 | Migdal et al. | 356/603 |
| 6,965,690 B2* | 11/2005 | Matsumoto | 382/154 |
| 7,197,179 B2* | 3/2007 | Rubbert et al. | 382/154 |
| 7,200,262 B2* | 4/2007 | Sawada | 382/154 |
| 7,978,892 B2* | 7/2011 | Quadling et al. | 382/128 |
| 2003/0071194 A1* | 4/2003 | Mueller et al. | 250/208.1 |
| 2006/0050952 A1* | 3/2006 | Blais et al. | 382/154 |
| 2007/0081718 A1* | 4/2007 | Rubbert et al. | 382/154 |
| 2008/0273773 A1* | 11/2008 | Ernst et al. | 382/128 |
| 2009/0268208 A1* | 10/2009 | Ertl | 356/479 |
| 2010/0209002 A1* | 8/2010 | Thiel et al. | 382/206 |

FOREIGN PATENT DOCUMENTS

| | | |
|---|---|---|
| DE | 44 16 108 C2 | 11/1995 |
| DE | 197 47 061 A1 | 5/1999 |
| EP | 0 160 797 A1 | 11/1985 |
| WO | 93/03579 A1 | 2/1993 |
| WO | 2004/085956 A2 | 10/2004 |
| WO | 2009/024756 A1 | 2/2009 |

* cited by examiner

METHOD FOR OPTICAL MEASUREMENT OF THE THREE DIMENSIONAL GEOMETRY OF OBJECTS

CROSS REFERENCE TO RELATED APPLICATIONS

This application is a continuation of International Application No. PCT/EP2008/065626, filed Nov. 14, 2008, and claims priority to German Patent Application No. 10 2007 054 906.9, filed Nov. 15, 2007 and U.S. Provisional Patent Application No. 60/988,570, filed Nov. 16, 2007, each of which is incorporated by reference herein in its entirety, as if set forth fully herein.

TECHNICAL FIELD

The invention relates to a method for optical measurement of the three dimensional geometry of objects and is concerned with the problem of camera-shake induced in 3D data of scanned objects acquired using stripe projecting methods and with the task of 3D scanning when there is relative motion between the camera and the object when being scanned, particularly for dental purposes.

PRIOR ART

Digital design data for the computer-assisted production of dental prosthetic items without having to create the usual impression can be acquired by optically scanning one or more teeth in a patient's mouth.

For such scanning, use is frequently made of measuring methods based on the principle of triangulation. Phase-shifting triangulation is disclosed in EP 0 160 797, in which a three dimensional data set is acquired from a sequence of images of a pattern which is displaced from image to image.

With prior triangulation methods, a single straight stripe of light is projected by a projector onto the object being scanned and the projected image is recorded by a camera at a parallax angle γ in the direction of observation, so as to produce an image P.

Depending on the surface structure of the object, the light stripe appears no longer to be straight, but curved and displaced with respect to its straight form. The surface structure of the object being scanned may then be concluded from the position and shape of the light stripe.

By moving the light stripe transversely to the direction of orientation of the light stripe, the entire object can be scanned to produce images P1 to PN. The relief data of the scanned object acquired from each individual image can be stored in the form of a two-dimensional pattern in the memory of a computer, which corresponds to a projection of the relief information of the surface of the scanned object onto a base surface as the reference surface. Following the scanning operation there is obtained a digital, three-dimensional data model of the scanned object, which can be displayed, for example, on a screen as a video still.

A method for the production of a three-dimensional image of an object is disclosed in WO 2004/085956 A2, a procedure which improves the above-described scanning method in that the surface structure of the scanned object is measured virtually simultaneously with the exposure Pi.

The light stripe can be produced, for example, by the rapid movement of a laser beam throughout the period of image creation (the exposure) such that the light stripe is actually composed of points of light. During an exposure Pi, the pinpoint light beam of a laser is directed over the object being scanned, along a 2-dimensional pattern for the light stripes, in which at least some of the light stripes are substantially parallel to each other, i.e. extend in a direction R1. Space is provided between the light stripes.

During an exposure, the relief data of the object being scanned are collected along a plurality of parallel, spaced light stripes or sections thereof.

Thus the image obtained already provides the relief data of the object being scanned in a first group of a plurality of spaced lines of the two-dimensional pattern of the yet to be produced three-dimensional data set.

Thereby the tangential vector at the light stripe sections is not perpendicular to the plane of triangulation, which is defined by the direction of projection and the direction of imaging.

During the next exposures, the laser beam is guided along preferably the same light stripe pattern, but with spatial parallel displacement relative to the previous image in a direction at right angles to the direction of orientation of the parallel light stripes into the space following the previous image, so that each image covers a different, neighboring portion of the object being scanned. Thus, each image provides the relief data of the object being scanned in another group of spaced lines of the two-dimensional pattern.

The entire object can be scanned by the laser by implementing a plurality of appropriately matching images having light stripe patterns each offset approximately at right angles to the direction of orientation of the light stripes, until, after a plurality of scans, the entire surface of the object to be scanned has been covered. In order to achieve the desired precision of the surface scan, an adequate number of image slices that lie sufficiently close to each other must be produced. By merging the images there are obtained the relief data of the object being scanned for each line of the two-dimensional pattern.

The independent relief data acquired from the individual images are merged in the two above-described procedures involving stripe projection which is quasi-static during each exposure, with one stripe per exposure or with a plurality of discrete stripes per exposure, as is known from WO 2004/085956 A2, thus forming an overall image describing or containing all of the 3D data of the object being scanned.

If a change in the orientation between camera and object occurs between the individual exposures, for example due to camera-shake, the coordinate systems of the individual images will no longer be the same. Since the change in the orientation between camera and object is, however, unknown, the two-dimensional patterns of the images Pi cannot be correctly merged to form a common 2-dimensional pattern of the overall image, which, for example, is chosen so as to be the same as the coordinate system of the first exposure.

For such scans, camera-shake means that the slices of the object being scanned measured in the individual exposures are no longer parallel to one another from one exposure to the next.

When the relief data contained in the lines of the 2-dimensional patterns of the blurred individual images are merged to form a common 2-dimensional pattern, an erroneous surface structure of the object being scanned will be obtained.

To make it possible to correctly integrate the images to nevertheless form a common 2-dimensional pattern and to obtain therefrom a correct three-dimensional image of the object being scanned, it is necessary to determine the coordinate transformations that reproduce the coordinate systems of the individual images in a common coordinate system. In order to do this, it is necessary to know the orientation and/or position of the two-dimensional pattern of the individual images relative to each other.

A dissertation by J. Gühring, "3D Erfassung and Objektrekonstruktion mittels Streifenprojektion" (University of Stuttgart, 2002) describes how a possible means of compensating for camera-shake exists in minimizing the surface of the object described by the combined image P. Such minimization or a similar process would be well suited for homogenous surfaces, such as that of a plane or a sphere, but would only be of limited use for scanning objects with pronounced topography, such as teeth.

The present problem is to provide a method for creating a three-dimensional image of an object being scanned, particularly for dental purposes, which produces a sufficiently accurate 3D model even if camera-shake takes place.

SUMMARY OF THE INVENTION

This object is achieved by the following characteristics of the invention.

According to the invention, a method for optical measurement of the three-dimensional geometry of an object by means of triangulation in which a pattern is projected onto the object being scanned in order to obtain a 3D data set. The projected pattern is recorded in each image. In a first step for the creation of at least one first image, a first pattern is projected, and in a second step for the creation of at least one further image, a further pattern deviating from the first pattern as regards position or shape is projected onto the object being scanned and in each case an image is created. In a subsequent step, the 3D data acquired from the first image and the following images are combined and merged into a 3D data set. The first image of the pattern projected onto the object being scanned and then recorded and the further image of the further pattern projected onto the object and recorded, are oriented with respect to one another in such a way that the two patterns partially overlap and comprise at least one common point on the object being scanned that is present in both recorded patterns. The 3D data acquired from these images are merged on the basis of the 3D data of the at least one common point recorded in both images to form a 30 data set such that the 3D data acquired from the images agree at least with reference to the 3D data of said common point in the 3D data set.

The triangulation method used in the present invention is based on the following principle.

A specific point of measurement on an object being scanned is illuminated from one direction by a projected beam and monitored from another direction by a sensor.

Thus there are two angles between the baseline (connecting the light source and the sensor) and the projected beam and monitoring beam respectively. Knowing the length of the baseline, it is possible to determine the coordinates of the measured point with respect to the coordinate system of the scanning apparatus comprising the light source and the sensor.

Advantageously, the present invention utilizes the stripe projecting method, in which a pattern of parallel stripes is projected onto the object being scanned, by which means a plurality of points of measurement can be scanned simultaneously.

In order to determine the coordinates of the point of measurement, one projection coordinate must be known that assigns a point of measurement to an image coordinate on the sensor. The points of measurement must be assigned in each of the light stripes.

Such assignment can be effected by counting the stripes by evaluating the sequence of brightness values registered on the sensor, so as to determine the number of each individual stripe.

This assignment can alternatively be accomplished using a binary code method (Gray code, for example), in which each stripe contains a binary sequence of brightness values representing the number of the stripe. By reading and interpreting this code, it is possible to determine the number of each stripe.

A higher degree of precision for the assignment of projection coordinates can be obtained using the so-called phase shift method, but this does not apply in the present invention, since, in the phase shift method the 3D data of the object being scanned can only be generated after reading at least four individual phase-shifted images.

The advantage of assigning by counting and using the binary code method resides in the fact that the 3D data for the area illuminated by the pattern can be generated immediately after each individual exposure.

The pattern can be composed of a single stripe or a plurality of parallel stripes.

The second pattern deviates from the first in its position or its shape. The second pattern may, for example, be rotated through a specific angle relatively to the first pattern or be displaced in a particular direction, or have a different shape.

If the first and second patterns are composed of parallel stripes, and the second pattern is displaced with respect to the first in a direction at right-angles to the direction of orientation of parallel stripes and is also rotated through a certain angle, then intersecting points will arise that are illuminated by both the first and the second pattern. These common points in the two resulting images are used as correlating points in order to combine the 3D data of both images to form a single 3D data set.

The rotation of the second pattern with respect to the first can be achieved by manually turning the scanning apparatus about the point of measurement between the first and second exposures, or by turning the grid in the scanning apparatus that produces the pattern.

One advantage of this method of the invention is that, unlike conventional methods, it corrects the errors that are caused by shaking movements of the hand-held scanning device. This is especially advantageous for dental intra-oral cameras, which are hand-held and used to generate 3D data sets of tooth surfaces. Camera-shake causes the resulting 3D images to show defects such as pointed or stepped structures, and the 3D scan must be repeated.

The overlapping of the common points allows the changes in position of the pattern caused by camera-shake to be identified and compensated for.

Another advantage is that the method of the invention makes on-the-fly measurement possible. The scanning device can be moved smoothly relatively to the object being scanned and the individual images scanned from different directions can be combined to form a complete 3D data set. It is thus not necessary to hold the scanning device still during an exposure. A sequence of exposures can be made without interruption while the scanning device is being moved relatively to the object.

Advantageously, more than two exposures can be made in further steps, and by utilizing the common points of the resulting images, the 3D data acquired can be combined to form a single 3D data set.

One exposure can thus be made in the first step, for example, and after turning the pattern, a further four exposures can follow, in which the width of the stripes is one quarter of the distance between the stripes, and the pattern is displaced relatively to the parallel stripes by the width of a stripe, transversely to the direction of orientation of the stripes so that the surface of the object being scanned is fully covered.

Advantageously, the relative position of the 3D data from the at least one further image can be determined with respect to the first scanned image on the basis of the 3D data of the at least one common point. On the basis of this relative position, a position correction of the 3D data of at least one further image can be undertaken. The corrected 3D data of the at least one further image and the 3D data of the first image are combined to form a single 3D data set.

By this means, the image defects that are caused by unsteady movement of the scanning device are corrected. The common points are implemented as correlation points, in order to determine the relative positions of the 3D data acquired from the various images. With knowledge of the relative positions, position correction of the 3D data is carried out, e.g. by coordinate transformations such that the common points are in register.

Advantageously, the position of the at least one common point, as recorded on at least two of the patterns on the object being scanned, can be discerned in the 3D data of the image by using a search algorithm.

By this means the common points of the various images will be automatically identified. The search algorithms of the image processing application are able to determine, on the basis of the characteristic shape of the individual images, their position on the surface of the object being scanned.

Advantageously, the ICP method or topology matching method can be used as a search algorithm to identify the at least one common point.

The ICP (Iterative Closest Point) method is used for the evaluation of 3D data that are similar in form in at least some regions.

The method use in image processing is the topology matching method, which uses MRGs (Multiresolutional Reeb Graphs) for the comparison of different topologies. MRGs are especially well suited as search criteria for similar 3D data sets. The computation of such similarity takes place quickly and efficiently with this method, since it necessitates no computation of the change of position or of any rotation.

Advantageously, the first pattern can show parallel stripes extending in one direction and the further pattern parallel stripes extending in another direction, in which case the said second direction of the parallel light stripes of said further pattern encloses with the first direction of the parallel stripes of first pattern a prescribed angle α of at least 5° and at most 90°. The common points are then formed by the points where the light stripes of the patterns intersect.

This ensures that the two patterns intersect and that common points are formed at the points of intersection. Localization of the points of intersection is facilitated when the angle is greater than 5°, while the points of intersection can be best discerned at an optimal angle of 90°.

Advantageously, the light stripes of said further pattern containing light stripes extending in the second direction can show greater spacing between individual stripes than the light stripes of the first pattern containing light stripes extending in the first direction.

In this way, the points of intersection can be more easily identified, since a greater distance between the individual stripes facilitates the analysis of the brightness values.

Advantageously, at least one exposure can be made of a first group to give an image containing a pattern having light stripes extending in substantially the first direction and that at least one exposure is made of a second group to give an image containing a pattern in which the light stripes extend in another direction which differs from the first by an angle α of >5°.

The resolution of the 3D data set is thereby improved. For example, one exposure can be made in the first direction, and a series of exposures in the second direction, the pattern being displaced in each case by the width of one stripe, with the result that the surface of the scanned object is completely scanned. Each striped pattern in the second group in the second direction will contain points of intersection with the individual images in the first group. As a consequence, positional correction can be carried out for each image.

Advantageously, the at least second group of images containing light stripes extending in the second direction can have a smaller group size than the first group of images containing light stripes extending in the first direction.

Advantageously, the distance between the light stripes for a group of images with uniformly oriented light stripes extending in direction R1 or R2 can be larger than the width of the light stripes by an integral factor.

The width of the individual light stripes determines the resolution of the 3D data. To achieve higher resolution, more images must be produced. The distance between the light stripes is several times the width of the stripes, since in the case of exposures made in the same direction the pattern is in each case displaced by the width of a light stripe transversely to the direction of orientation of the light stripes. For example, the distance between the light stripes is four times the width of a light stripe and will require four exposures.

Advantageously, the angle α between the first and second directions is 90°.

An angle of 90° is best for computer-assisted localization of intersecting points.

Advantageously, the direction vectors of the first and second direction R2 of the pattern can be at an angle of greater than 30° and at most 90° with respect to a plane of triangulation predefined in the triangulation method.

The plane of triangulation is defined by the projected beam and the monitoring beam. For error-free functioning of the stripe projecting method, the angle between the direction vectors of the light stripes and the plane of triangulation must be greater than 0° and is advantageously at least 30°. An angle of 90° is best suited for the creation of images.

Advantageously, the first and second directions can enclose with the plane of triangulation an angle β and an angle γ of up to +60° or −60° respectively.

Thus the angle α between the first and second directions is sufficient for precise determination of the intersecting, points and the angles β and γ between the first and second directions and the plane of triangulation respectively are sufficient for error-free functioning of the stripe projecting method. The method of the invention is particularly advantageous when the angle α is 90°, the angle β is 45°, and the angle γ is 45°.

Advantageously, the first and further images can cover the same area of measurement of the object.

This ensures that the common points between the two patterns can be identified.

Advantageously, the first and further exposures or the first and further groups of exposures can be made at time intervals of at least 100 ms.

In this way camera-shake between exposures is minimized.

Advantageously, the pattern can be rotated through an angle α by mechanically adjusting a grid inside the scanning device.

The grid can be turned so as to adjust the direction of the light stripes accurately by the desired angle α. This makes it possible to adjust the direction of orientation of the light stripes by a prescribed angle α, which should be as close to 90° as possible.

Advantageously, the pattern can be turned through an angle α by turning the entire scanning device.

Consequently, the scanning device can be turned through an angle α manually after the first group of exposures has been made in order to make a second group of exposures in which the light stripes intersect those of the first group of exposures. The scanning device should in such cases be turned through an angle α as close to 90° as possible. This embodiment has the advantage over the embodiment using the adjustable grid that the angles β and γ between the light stripes and the plane of triangulation remain the same, since the entire device is turned, and can advantageously be 90°.

Advantageously, the first pattern can be partially overlapped by the further pattern and have at least three points common to both patterns on the object being scanned.

Positional correction is facilitated with a higher number of common points.

The invention also relates to an alternative method for optically scanning the three-dimensional geometry of an object by means of triangulation, wherein a pattern is projected onto the object being scanned in order to obtain a 3D data set and wherein the pattern is recorded in an image. In a first step for the production of at least one first image, a first pattern is projected onto the object being scanned, and in a second step for the production of at least one further image, a further pattern that deviates from the first as regards orientation or shape is projected onto said object and the image is produced, and the 3D data acquired from the first image and those from the second image are combined in a subsequent step to form a 3D data set. Furthermore, at least one correlating exposure is made using a correlating pattern that is projected onto the object being scanned, the resulting correlating image and the first image of the first pattern projected onto the object being scanned and the resulting further image of the further pattern projected onto the object being scanned are oriented with respect to one another in such a way that said first and second images each show at least one common point with the correlating image, which is recorded in the images containing the two patterns. The 3D data acquired from the images are merged, on the basis of the 3D data of the at least one common point in the images and in the correlating image, with the said 3D data set such that the 3D data acquired from the images at the common point in the 3D data set will agree with the 3D data acquired from the correlating image.

In contrast to the first embodiment, a correlating exposure is made in addition to the two scanning exposures, and positional correction is carried out with reference to the intersecting points between the pattern in the correlating image and the patterns in the first and second images.

An advantage of this procedure is that a series of exposures can be made with constant orientation of the light stripes, but each displaced by the width of a single light stripe, in order to completely scan the surface of the scanned object, and then a correlating exposure can be made with the light stripes oriented in another direction such that the light stripes in the resulting correlating image intersect those in the resulting first and second images. Positional correction can then be made on the basis of the common points.

Advantageously, more than two images can be produced and, with utilization of common points in the correlating image, the resulting 3D data can be combined to form a single data set.

Thus, for example, four images can be produced in the first step and, after rotating the pattern, a correlating image can be produced. The distance between the stripes would then be four times the width of a stripe, in order to completely cover the surface of the scanned object.

Advantageously, the 3D data of the at least one common point in the image and the 3D data of the common point in the correlating image can be implemented to determine a positional relationship between the 3D data of the image relative to the 3D data of the correlating image. Positional correction of the 3D data from the image is effected on the basis of said positional relationship. The corrected data acquired from at least two images are then combined to provide a 3D data set.

By this means, imaging errors that arise from unsteady movement of the scanning device are corrected. The common points shared by the images and the correlating image are utilized as correlating points in order to determine the positional relationship between the 3D data acquired from the various images. When the spatial relationship is known, a positional correction of the 3D data is carried out, for example by means of coordinate transformations, such that the common points are in register with each other.

Advantageously, the actual position of the at least one common point in the 3D data of the image, on one hand, and the 3D data of the correlating image, on the other, can be identified by a search algorithm.

In this way the common points in the various images will be automatically identified.

Advantageously, the first pattern and the further pattern can be free of overlap.

This ensures that the further patterns in the first group of images will be parallel to the pattern in the first image but with each displaced by the width of a stripe, such that the entire surface of the scanned object is scanned.

Advantageously, the first and further patterns can have parallel stripes orientated in a first direction.

As a result, the orientations of the first and second patterns will agree.

Advantageously, the parallel stripes of the further pattern can be displaced with respect to those of the first pattern.

Consequently, the entire surface of the object being scanned can be covered by a minimum number of images. Advantageously the pattern will be displaced by the width of a stripe.

Advantageously, the light stripes of the further patterns and those of the first pattern can be separated from each other by a distance several times the width of a single stripe.

The width of a single light stripe determines the resolution of the 3D data. Thus to achieve higher resolution, more images must be produced.

Advantageously, the correlating pattern can contain light stripes extending along a second direction that differs by a prescribed angle α of at least 5° and at most 90° relative to the first direction in which the first and further images are oriented. The common points are then formed by the intersection points between the light stripes in the pattern in one image and the light stripes in the correlating pattern in the correlating image.

This ensures that the two patterns intersect and that the common points are formed by the intersecting points.

Advantageously, the correlating image of light stripes extending in a second direction can display a greater distance between the light stripes than the first and further images extending in the first direction.

The increased spacing between the light stripes makes for more efficient recognition of the intersection points by evaluating differences in the brightness values.

Advantageously, the angle α between the first and second directions can be equal to 90°.

The intersecting points can be best identified at an angle α of 90°.

Advantageously, the direction vectors relating to the first direction of the patterns for the images and relating to the second direction of the pattern for the correlating image can be at an angle greater than 30° and not more than 90° with respect to a plane of triangulation predefined by the triangulation method.

The plane of triangulation is formed by a projected beam that is projected onto a point of measurement and a monitoring beam that leads from the point of measurement to a sensor. The stripe projecting method requires an angle of at least 30° between the direction of the stripes and the plane of triangulation, an angle of 90° being advantageous.

Advantageously, the first direction of the images can enclose an angle β with the plane of triangulation, and the second direction of the correlating image can enclose an angle γ of up to +60° or −60°.

Thus the angle α between the first and second directions is sufficient for precise determination of the intersecting points and the angles β and γ between the first and second directions and the plane of triangulation respectively are sufficient for error-free functioning of the stripe projecting method. This method of the invention is particularly advantageous when the angle α is 90°, the angle β is 45°, and the angle γ is 45°.

Advantageously the pattern of the at least one image can be partially overlapped by that of the correlation pattern for the correlating image and have at least three points common to the pattern and the correlating pattern on the scanned object.

Positional correction is facilitated by a higher number of common points.

The basic principle lies in obtaining appropriate, partially redundant data with which it is possible to reconstruct the relative positions of the two-dimensional patterns in the individual images. If these relative positions are known, it is possible to merge the relief data acquired from the individual images to form a suitable overall image.

The redundant data should be such that the demands on memory storage and the time required for data acquisition are both minimized by using the least possible amount of data to give the highest possible degree of correlation between the individual images.

The invention is based on the idea that during the production of at least one of the individual images, the object being measured is scanned by one or more light stripes that are substantially oriented in a second direction, which differs substantially by a non-zero angle α from the first direction in which the light stripes in the other individual images are substantially oriented.

This at least one image can be one of those in which the pattern extends in another direction or a correlating image. In the first case all of the 3D data acquired from all of the images are combined to form a data set. In the second case the correlation image is used only to identify the intersecting points and to carry out the positional correction.

Since the at least one exposure covers the same region on the object as in the other exposures, the same points of the object being measured are present in the 3D data acquired from the at least one image as are present in the other images. Specific points on the surface of the object, namely those where there is intersection of the light stripes of the two-dimensional pattern of the at least one image and those of the two-dimensional pattern of the other images, are therefore imaged at least twice. These intersecting points are referred to as the common points.

On the basis of these common points it is possible to establish correlation between the relative position of the two-dimensional patterns of all of the images, since the angle α between the at least one image and the other images is known except for the portion caused by camera-shake. After suitable adjustment and adaptation of the two-dimensional patterns such that the best possible agreement of the relief information at the common points of any pair of images consisting of the correlating image and one of the other images is obtained, the 3D data acquired from the individual images can be combined to form a single 3D data set.

BRIEF DESCRIPTION OF THE DRAWINGS

Exemplary embodiments of the invention are illustrated in the drawings, in which.

EXEMPLARY EMBODIMENTS OF THE INVENTION

Figure 1:
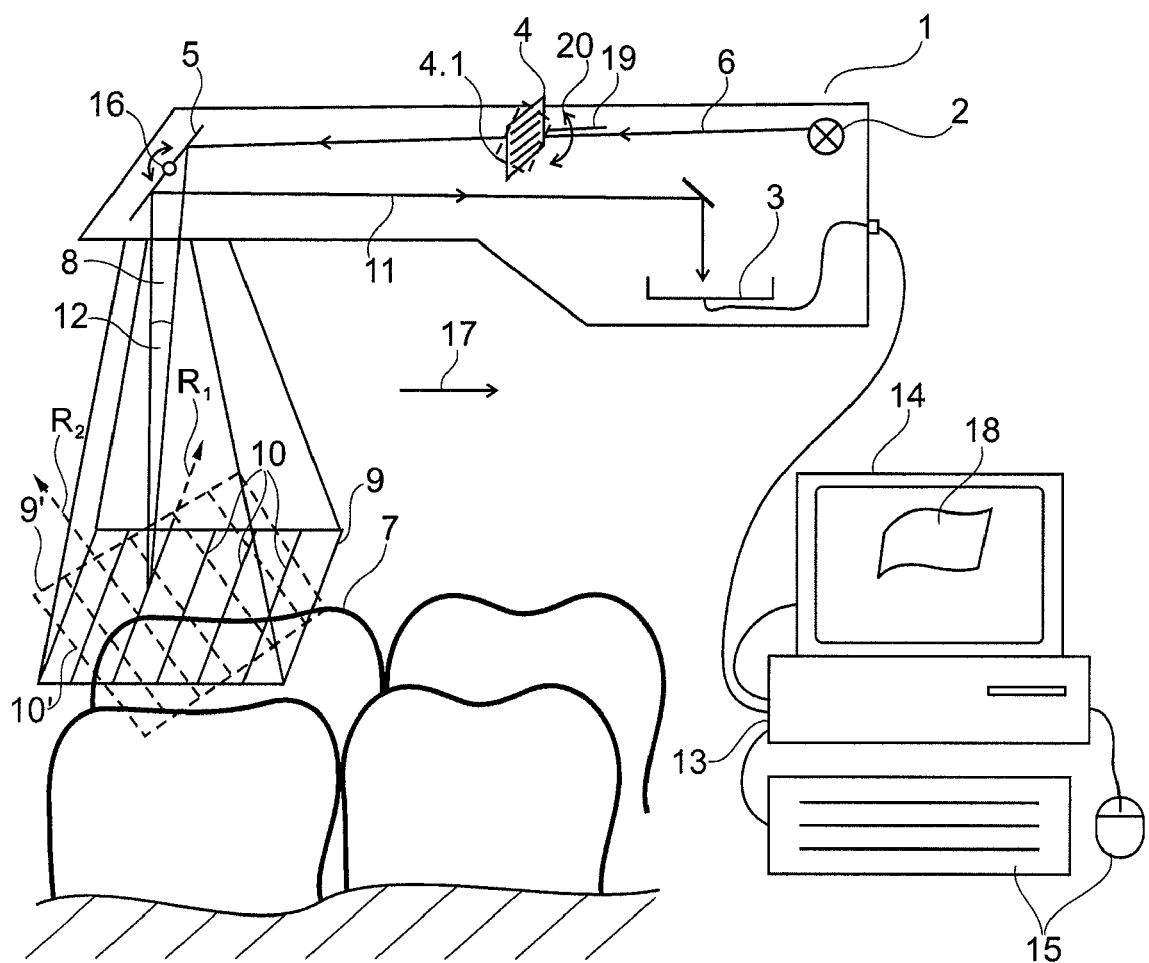
FIG. 1 is a sketch illustrating the method of the invention, showing an intraoral dental camera and a scanning device for scanning teeth.

FIG. 1 shows an intraoral dental camera as scanning device 1, which is equipped with a light source 2, a sensor 3, a grid 4, and a pivoted mirror 5. The light source 2 emits a projected beam 6 that passes through the grid 4 and is directed by the pivoted mirror 5 onto the object 7, namely the surface of a tooth to be scanned. The grid 4 has a slit 4.1 that is perpendicular to the plane of triangulation 8, so that a structured pattern 9 comprising parallel stripes 10 is projected onto the surface of the object 7 to be scanned. The structured pattern 9 is only diagrammatically illustrated and does not represent the actual projection of light stripes 10 on the object 7 to be scanned. The projected beam 6 is reflected by the surface of the object 7 and is back-projected as a monitoring beam 11. The monitoring beam 11 is directed to the sensor 3 and detected thereby. The plane of triangulation 8 is defined by the projected beam 6 and the monitoring beam 11. The projected beam 6 encloses with the monitoring beam 11 a so-called triangulation angle 12. The image data acquired by the sensor are sent to a computer that functions as an evaluating unit 13, which has a monitor as display unit 14, and a keyboard and mouse functioning as inputting units 15.

The pivoted mirror 5 can be pivoted about an axis 16 and the pattern 9 thereby incrementally moved in the direction 17 in the plane of triangulation 8. With the method of the present invention a plurality of images with the pattern 9 being moved between each exposure by a stripe's width in the direction 17 until the surface of the object 7 has been scanned completely. 3D data are computed from each individual image by means of the evaluating unit 13. Such computation is effected using the principle of triangulation, in which the coordinates of a point of measurement relative to the coordinate system of the scanning device are determined from the two angles between a baseline, connecting light source and sensor, and the projected beam and the monitoring beam respectively and the length of the base length.

The 3D data acquired from the individual images are then combined to form a single 3D data set, which is displayed on the display unit 14 as a 3D picture 18.

In traditional triangulation procedures, camera-shake of the scanning device 1 caused by the user during a scan causes defects in the image, which appear as pointed or stepped structures in the 3D picture 18. These defects arise because the change in position of the pattern between the individual exposures is not taken into account when combining data to form the complete 3D data set.

The method of the present invention solves this problem by effecting a positional correction for each individual image. This is done as follows: the grid 4 can be switched in a direction 20 about an axis 19 of the grid. When the grid 4 is switched about the axis 19, the projected pattern 9 is also rotated relatively to the object being scanned 7. As a consequence, a plurality of images is produced with the light stripes 10 of the pattern 9 extending in a first direction R1 in order to cover the surface of the object 7 completely and then the grid 4 is switched back and a further image is produced in a second direction R2 of the light stripes 10' in the pattern 9'. This further image shows intersecting points with the previously produced images and is used for positional correction.

Figure 2:
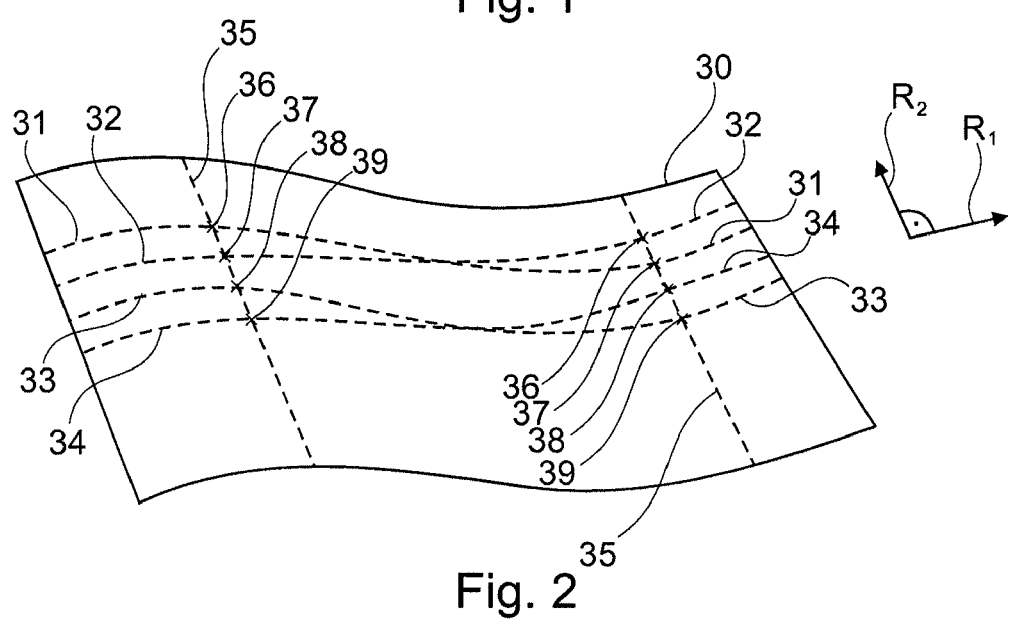
FIG. 2 shows a region of the surface of an object being scanned depicting five images of differing orientation.

FIG. 2 is a diagrammatic representation of a region of the surface of an object 7 to be scanned, in which the first four images 31, 32, 33, and 34, which are represented by dash lines showing the actual direction of the parallel light stripes 10 of the pattern 9 on the object 7, are produced in the first position of the grid 4 in the direction R1, after which an further image 35 is produced, represented here by the dash line depicting the orientation of the light stripe pattern, which image is produced with the grid 4 positioned in the direction R2 after switching it through an angle α of 90°.

Whenever the scanning device 1 is shaken by the user, the projected pattern 9 is also shaken such that the light stripes in images 31, 32, 33, and 34 are not parallel to each other and partly overlap. The light stripes in the image 35 intersect those in images 31, 32, 33, and 34, the 3D data of the intersection points 36 being recorded in both image 31 and image 35. In the intersecting points 37 the 3D data of images 32 and 35 are recorded. The 3D data of the intersecting points 38 are recorded in images 33 and 35. The 3D data of the intersecting points 38 are recorded in images 34 and 35. These intersecting points are consequently the common points of the individual images 31, 32, 33, and 34 present in image 35. After the common points 36, 37, 38, and 39 have been identified in the individual images 31, 32, 33, and 34, the relative positions of the images with respect to each other are determined, and positional correction is carried out in order to compensate for those imaging defects arising from shaking of the scanning device 1 by the user.

Figure 3:
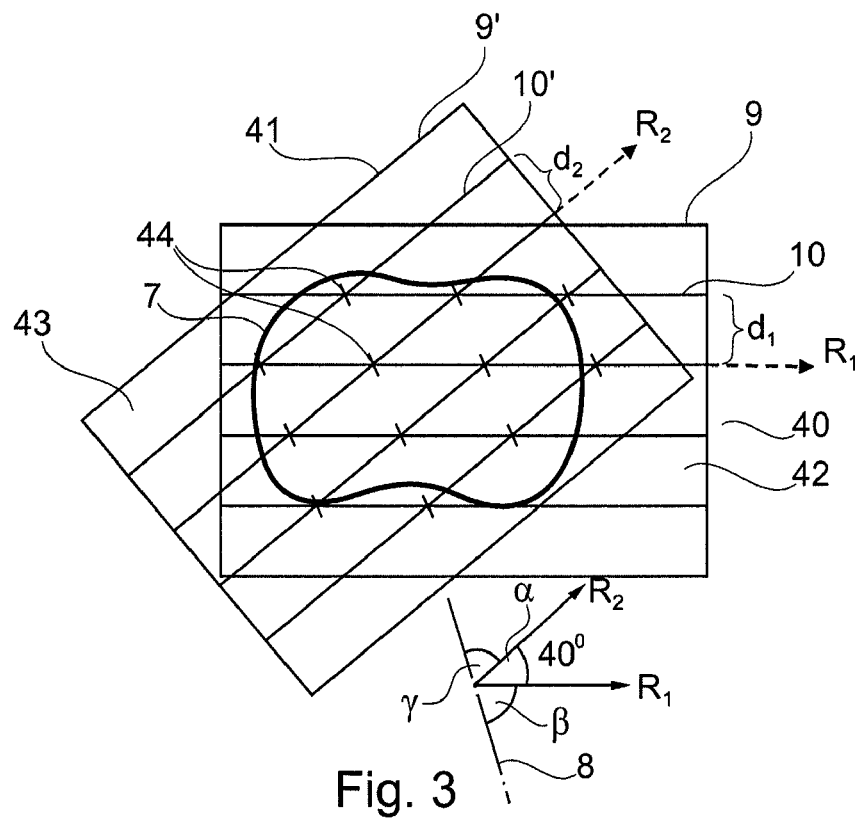
FIG. 3 is a diagrammatic illustration of the patterns in two images with an angle α of 40° between the first and second directions.

FIG. 3 is a diagrammatic representation of a first image 40 showing a first pattern 9 whose light stripes 10 are oriented in the direction R1 and of a second image 41 showing a second pattern 9' whose light stripes 10' are oriented in a second direction R2. The angle α between the first direction R1 and second direction R2 is 40°. The object 7 to be scanned, namely a tooth, can be seen in top view. The object 7 is located such that it lies both inside the area of measurement 42 of the first image 40 and inside the area of measurement 43 of the second image 41. The light stripes 10 of the first pattern 9 intersect the first stripes 10' of the second pattern 9' at the intersecting points 44, which are the common points in images 40 and 41. On the basis of these common points 44 the relative position of the second image 41 with respect to the first image 40 can be determined and the 3D data acquired from the images 40 and 41 can, taking into account the relative positions, be combined to form a single 3D data set. The first distance d1 between the light stripes 10 in the first image 40 and the second distance d2 between the light stripes 10' in the second image 41 are the same.

For each of the images 40 and 41 in the directions R1 and R2, the light stripes 10 and 10' may not be parallel to the plane of triangulation 8 shown in FIG. 1, this being a prerequisite for correct functioning of the stripe projecting method based on the triangulation method. In the present case the angle β between the plane of triangulation 8 and the direction R1 is 45° and the angle γ between the plane of triangulation 8 and the direction R2 is 45°.

Figure 4:
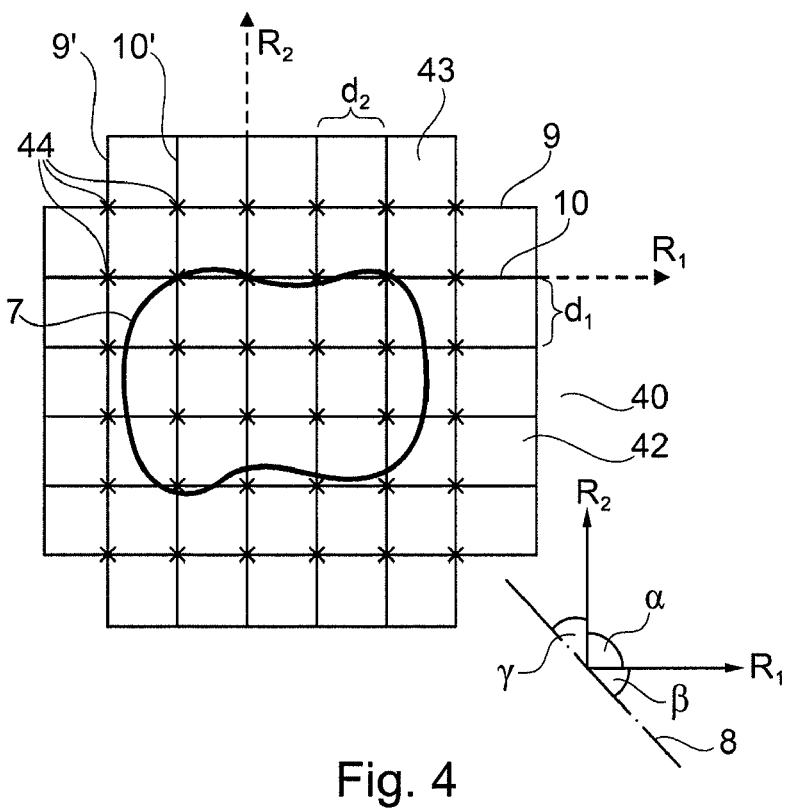
FIG. 4 is a diagrammatic illustration of the patterns of two images with an angle α of 90° between the first and second directions.

FIG. 4, like FIG. 3 is a diagrammatic representation of a first image 40 with a first pattern 9 whose light stripes 10 are oriented in a first direction R1 and a second image 41 with a second pattern 9' whose light stripes 10' are oriented in a second direction R2. The angle α between the first direction R1 and the second R2 is 90°.

The intersecting points 44 correspond to similar points between the two images 40 and 41.

For each of the images 40 and 41, the tangential vectors of the scanning light stripes, that is, the directions R1 and R2 of the light stripes 10 and 10' may not be parallel to the plane of triangulation 8 shown in FIG. 1. In the present case the angle β between the direction R1 and the plane of triangulation 8 is 45° and the angle γ between the direction R2 and the plane of triangulation 8 is 45°.

It is also conceivable that in a first group G1 of images the light stripes are oriented substantially in a direction R1 and that in a second group G2 of images they are oriented substantially in a direction R2.

In general, any image, whether it belongs to a group of images with light stripes oriented in direction R1 or to a group with light stripes oriented in direction R2, may comprise one or more light stripes.

The distances d1 and d2 between the substantially parallel light stripes need not be the same for all images.

It is advantageous when the spacing between the light stripes in a group of images is the same in direction R1 or R2.

It is particularly advantageous when the group of images with light stripes oriented in the direction R2, which is used to record redundant data, shows greater spacing between the light stripes or has a smaller group size than the group of images with light stripes oriented in the direction R1, which is intended for precise measurement of the surface structure of the object being scanned.

The embodiment illustrated in which the angle α is 90° is the preferred embodiment, since the common points 44 can be best identified by means of computer-assisted analysis of the differences in brightness values when the angle α is 90°.

The embodiment in which the angle β is 45° and the angle γ is 45° is also a preferred embodiment, since these angles suffice for the successful use of the stripe projecting method.

Figure 5:
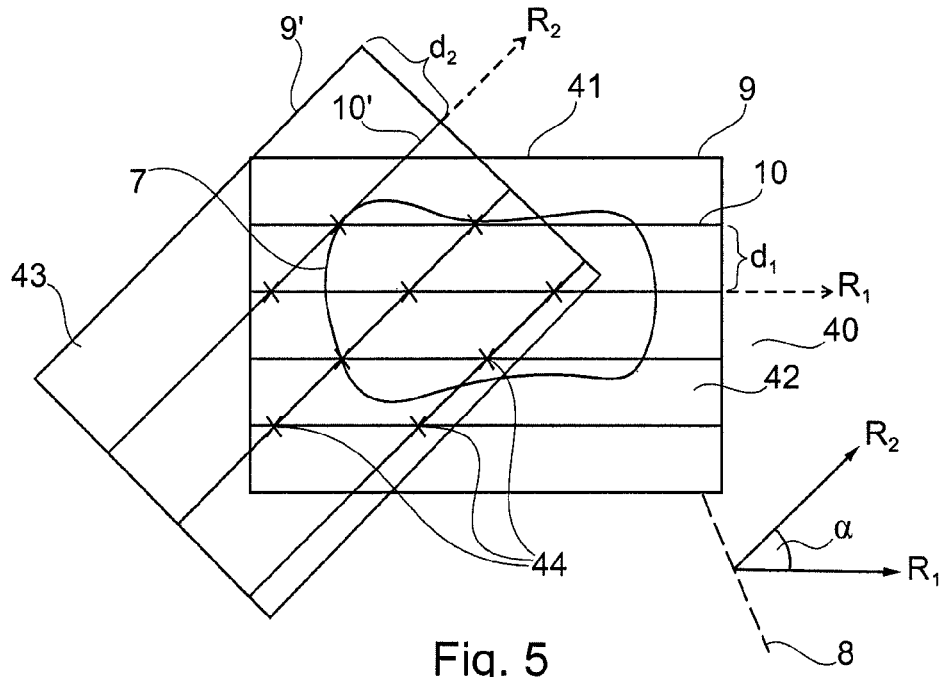
FIG. 5 is a diagrammatic illustration of a first pattern and of a second pattern of a second image at an angle α of 45°, the distance between the light stripes in the second pattern being larger than in the first pattern.

FIG. 5, like FIG. 3 and FIG. 4, shows two images 40 and 41, in which the angle α between the first direction R1 and the second direction R2 is 45°. The distance d2 between the light stripes 10' in the second image 41 is greater than the first distance d1 between the light stripes 10 in the first image 40. This preferred embodiment has the advantage that the second image 41 in the second direction R2 has a smaller number of light stripes 10' than the number of light stripes 10 in the first image 40. Thus a smaller number of intersecting points 44 need be computed. The second image 41 or a second group G2 of images in direction R2 serves merely as a correlate for positional correction, wherein the first image 40 or the first group G1 of images in the direction R1 serves to provide a precise measurement of the scanned object's surface structure.

Additionally, the area to be scanned on the object 7 is completely covered by the first pattern, whereas the second pattern 9' only partially covers the area to be scanned on the object 7. As a consequence, the intersecting points 44 are only in the overlapping region of the two images 9 and 9', which covers only a portion of the area to be scanned on the object 7. In spite of this, the positional relationship between the images 9 and 9' can still be determined on the basis of these intersecting points. It is therefore not necessary for the further image 41 in direction R2 to completely cover the area to be scanned in image 40.

Figure 6:
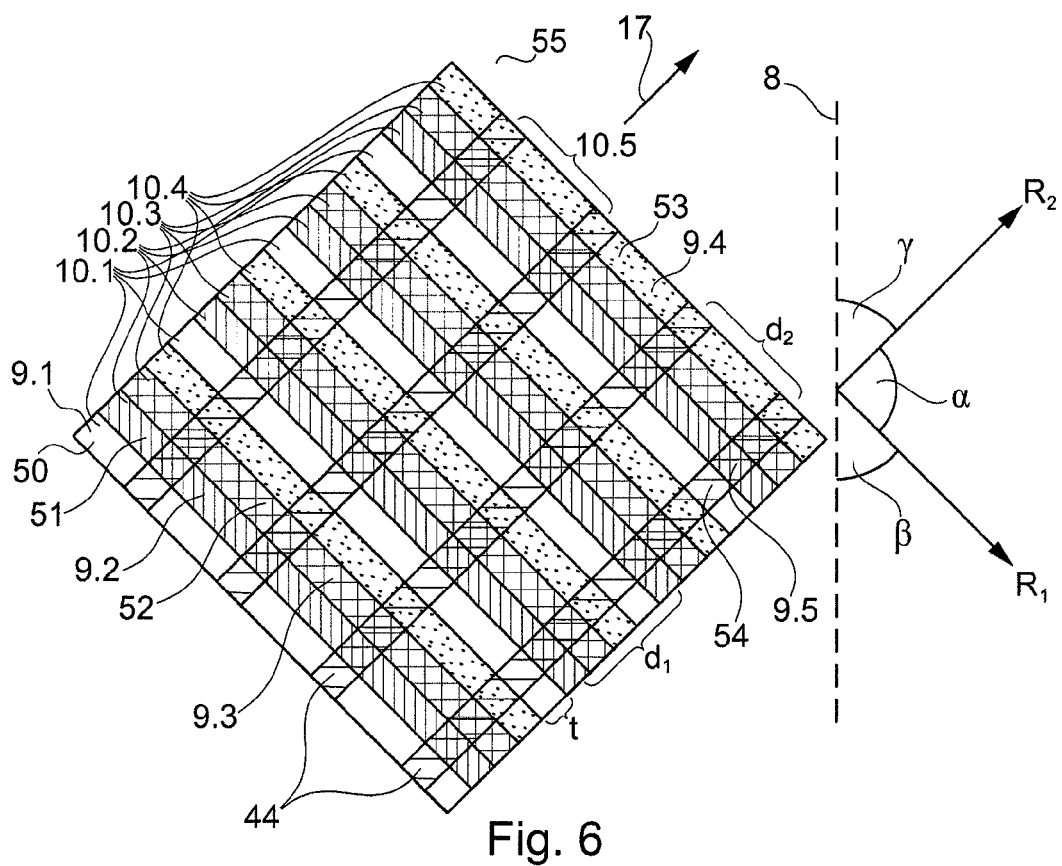
FIG. 6 is a diagrammatic illustration of the combination of four different images to form a single image with a correlating image in which angle α is 90° and the angles β and γ relative to the plane of triangulation are 45°.

FIG. 6 shows diagrammatically how four images are combined to form a single overall image. In the first image 50, the pattern 9.1 is in a first position and formed by the light stripes 10.1, which are oriented in a first direction R1. In the second image 51, the pattern 9.2 is in a second position and formed by the light stripes 10.2, which are oriented in direction R1 but are displaced with respect to the light stripes 10.1 by the width t of a stripe in the direction 17 shown in FIG. 1. In the third image 52, the pattern 9.3 is in a third position and is formed by the light stripes 10.3, which are oriented in the direction R1 but are displaced with respect to the pattern 9.2 by the width t of a light stripe in direction 17 shown in FIG. 1. In the fourth image 53, the pattern 9.4 is in a fourth position and is formed by the light stripes 10.4, which are oriented in the direction R1 but are displaced with respect to pattern 9.3 by the width t of a light stripe in the direction 17 shown in FIG. 1.

A correlating image is produced as a fifth image 54, whose light stripes 10.5 are oriented in the second direction R2. The angle α between R1 and R2 is 90°, while the angle β is 45° and the angle γ is 45°.

The distance d1 between the light stripes of the patterns 9.1, 9.2, 9.3, and 9.4 is four times the width t of a light stripe, so that the surface of the object being scanned 7 is completely covered by the four images 50, 51, 52, and 53. The fifth image 54 serves merely as a correlating image for the identification of the common intersecting points 44 for correlation of the first four images.

The second distance d2 between the light stripes 10.5 in the fifth image 54 is equal to the distance d1 in the embodiment shown, but may be larger.

Each individual image 50, 51, 52, and 53 therefore contains one quarter of the data present in the complete, combined image 55. Only the combination of the four images covers the total area to be scanned by the two-dimensional pattern 9 in the context of the given discretization.

The combination of the images 50, 51, 52, and 53 to form a fused image 55 is possible in a meaningful way and yields the correct surface of the object being measured 7 in the context of the given discretization only when there has been no camera-shake between these individual images 50, 51, 52, and 53, i.e., when there has been no significant change in the relative position between the scanning device 1 and the object 7 throughout the scanning operation, and the coordinate systems of the images 50, 51, 52, and 53 thus remain the same. Only then can a correlation between the 3D data in the light stripes 10.1, 10.2, 10.3, and 10.4 of the two-dimensional patterns in the individual images 50, 51, 52, and 53 be established and a common two-dimensional pattern fused to an overall image 55, containing the correct 3D data of the object being scanned 7.

If a change occurs in the positional relationship between the scanning device 1 and the object 7 between the production of the individual images 50, 51, 52, and 53, for example due to camera-shake, then the coordinate systems of the individual images 50, 51, 52, and 53 will no longer be the same. Since the change in orientation between the scanning device 1 and the object 7 is unknown, the two-dimensional patterns of the images 50, 51, 52, and 53 cannot be correctly fused to form an overall image 55 of the total area to be scanned.

For such scanning, camera-shake means that the slices of the object being scanned that are recorded in the individual images 50, 51, 52, and 53 are no longer parallel to each other from one image to the next. This is diagrammatically represented in FIG. 2. For example, during the second exposure 51, the portions of the object 7 are scanned along the light stripe 10.2 that have been rotated or displaced relative to the light stripes 10.1 of the first image 50. Consequently each image 50, 51, 52, and 53 contains a part of the 3D data of an object 7 that is slightly displaced or rotated.

If these data contained in the light stripes 10.1, 10.2, 10.3, and 10.4 of the two-dimensional patterns of the images 50, 51, 52, and 53 are combined to form a fused image 55, there is obtained an erroneous representation of the surface structure of the object 7.

These imaging errors can be avoided by positional correction. In order to do this, it is necessary to determine which coordinate transformations will reproduce the coordinate systems of images 50, 51, 52, and 53 on a common coordinate system. To this end, the relative orientations and/or positions of the two-dimensional patterns 9.1, 9.2, 9.3, and 9.4 in the individual images relative to each other must be known. This can be done by identifying the intersecting points 44, which serve as correlating points.

LIST OF REFERENCE NUMERALS OR CHARACTERS 1) scanning device
2) light source
3) sensor
4) grid
4.1) slit
5) pivoted mirror
6) projected beam
7) object to be scanned
8) triangulation plane
9) pattern
9') pattern
9.1) pattern
9.2) pattern
9.3) pattern
9.4) pattern
10) parallel light stripes
10') light stripes
10.2) light stripes
10.3) light stripes
10.4) light stripes
10.5) light stripes
11) monitoring beam
12) triangulation angle
13) evaluation unit
14) display unit
15) control unit
17) direction
18) 3D picture
19) grid axis
20) direction 30) section
31) image
32) image
33) image
34) image
35) image
36) intersection points
37) intersection points
38) intersection points
39) intersection points
40) first image
41) second image
42) area of measurement
43) area of measurement
44) intersection points
50) first image
51) second image
52) third image
53) fourth image
54) fifth image
55) overall image/overall 3D data set
R1) first direction
R2) second direction
d1) first distance
d2) second distance
G1) first group
G2) second group
t) width of light stripe

The invention claimed is:

1. A method for optically scanning a three-dimensional geometry of an object by means of a triangulation method, a pattern being projected onto the object to be scanned, in order to obtain a 3D data set and the projected pattern is recorded in an image, the method comprising:
projecting a first pattern on the object to be scanned, to create at least one first image;
projecting a second pattern, which deviates from the first pattern as regards position or shape, on the object to be scanned, to create at least one second image;
merging 3D data acquired from the first image and from the second image, to form a 3D data set;
projecting a correlating pattern onto the object to be scanned to create at least one correlating image,
wherein the correlating image, the at least one first image, and the at least one second image are oriented relatively to each other in such a manner that the at least one first image and the at least one second image each have, with the correlating image, at least one common point illuminated by both the correlating pattern and the first pattern or the second pattern, respectively, and recorded in the at least one first image or the second image, respectively, and the correlating image; and
merging the 3D data with the 3D data set, on the basis of 3D data acquired from the first image, the second image, and the correlating image, respectively, at the at least one common point, such that 3D data acquired from the first and second images at the at least one common point each agree with the 3D data acquired from the correlating image at the at least one common point,
wherein the first pattern and the second pattern exhibit parallel light stripes oriented in a first direction,
wherein the correlating pattern exhibits light stripes oriented in a second direction which differs by a given angle of at least 5° and not more than 90° with respect to the first direction in which the first and second patterns in the first and the second images are oriented,
wherein the at least one common point is formed by at least one point of intersection between the light stripes in the first or second pattern in the first or second image, respectively, and the light stripes in the correlating pattern in the correlating image,
wherein the correlating image containing light stripes oriented in the second direction shows greater spacing of light stripes than in the first and second images containing light stripes oriented in the first direction, and
wherein at least one of the above merging steps is performed by an evaluation unit.

2. The method according to claim 1, wherein more than two images are created and 3D data acquired therefrom are merged to form an additional 3D data set on the basis of the 3D data of the at least one common point.

3. The method according to claim 1, further comprising:
determining, on the basis of the 3D data acquired from the first image, the second image, and the correlating image, respectively, at of the at least one common point, a positional relationship between the 3D data and 3D data of the correlating image;
positionally correcting, on the basis of the positional relationship, the 3D data of the first and second images, to create corrected 3D data of the first and second images, respectively; and
merging, the corrected 3D data of the first and second images to form a corrected 3D data set.

4. The method according to claim 1, further comprising identifying, by means of a search algorithm, an actual position of the at least one common point in the 3D data acquired from the first image and the second image and in 3D data of the correlating image.

5. The method according to claim 1, wherein the first pattern and the second pattern are free of overlap.

6. The method according to claim 1, wherein the parallel light stripes in the second pattern are offset from the parallel light stripes in the first pattern.

7. The method according to claim 6, wherein the light stripes in the second pattern and the light stripes in the first pattern are spaced from each other by a distance necessary for a required resolution.

8. The method according to claim 6, wherein the angle between the first direction and the second direction is 90°.

9. The method according to claim 8, wherein direction vectors pertinent to the first and second directions of orientation in the patterns are at an angle greater than 0° and not more than 90° with respect to a triangulation plane defined by the triangulation method.

10. The method according to claim 9, wherein the first and second directions enclose with the triangulation plane a first angle and a second angle of up to +60° or −60°.

11. The method according to claim 9, wherein the pattern in the first or second image is partially overlapped by the correlating pattern in the correlating image and exhibits at least three common points on the object to be scanned which are recorded in the first or second image of the first or second pattern, respectively, and in the image of the correlating pattern.

* * * * *

UNITED STATES PATENT AND TRADEMARK OFFICE
CERTIFICATE OF CORRECTION

PATENT NO. : 8,280,152 B2  
APPLICATION NO. : 12/770426  
DATED : October 2, 2012  
INVENTOR(S) : Frank Thiel et al.

Page 1 of 1

It is certified that error appears in the above-identified patent and that said Letters Patent is hereby corrected as shown below:

ON TITLE PAGE AT (63) RELATED U.S. APPLICATION DATA:

Insert --Nov. 16, 2007 (US) ............. 60/988,570--.

Signed and Sealed this
First Day of October, 2013

Teresa Stanek Rea
*Deputy Director of the United States Patent and Trademark Office*